United States Patent [19]
Fromer

[11] Patent Number: 6,135,985
[45] Date of Patent: Oct. 24, 2000

[54] DISPENSER ARRANGEMENT FOR DISPENSING EYEDROPS

[76] Inventor: Mark D. Fromer, 115 E. 61st St., New York, N.Y. 10021

[21] Appl. No.: 09/287,828

[22] Filed: Apr. 7, 1999

[51] Int. Cl.[7] .................................................. A61M 35/00
[52] U.S. Cl. .......................................... 604/295; 222/420
[58] Field of Search ..................................... 604/294, 295, 604/296, 300; 222/420, 421, 422, 206, 207

[56] References Cited

U.S. PATENT DOCUMENTS 5,069,675  12/1991  Menchel et al. ......................... 604/295
5,462,200  10/1995  Weiler ....................................... 222/83
5,496,471   3/1996  Heyl et al. ............................... 222/420
6,041,978   3/2000  Hagele .................................... 222/420

*Primary Examiner*—Glenn K. Dawson
*Assistant Examiner*—David J. Cho
*Attorney, Agent, or Firm*—Cobrin & Gittes

[57] ABSTRACT

A dispenser of eyedrop medication that includes a detachable spout connected to a bottle. The spout has a curved bend region that terminates in a discharge port and that extends in a radial direction from a center of the mouth of the eyedrop bottle to define a distance less than one-half a width of the body of the eyedrop bottle or, if larger, then made of a flexible, resilient material. In this manner, a cap may be secured to the eyedrop bottle to contain the spout with the confines of the cap.

14 Claims, 5 Drawing Sheets

DISPENSER ARRANGEMENT FOR DISPENSING EYEDROPS

BACKGROUND OF THE INVENTION

1. Field of the Invention

The invention relates to eyedrop dispenser to dispense eyedrop medication through a curved spout from an eyedrop bottle.

2. Discussion of Related Art

Patients taking eyedrop medication have difficulties dispensing eyedrops into their eyes if the dispensement spout is concentric with the eyedrop bottle, because the eyedrop bottle blocks the patient's view of a mirror that would otherwise help the patient position the eyedrop bottle properly.

Such difficulties arising from dispensement of eyedrops is explained in U.S. Pat. No. 5,040,706, entitled LIQUID DROPLET DISPENSING APPARATUS. It reveals a reservoir 18 that is squeezed to eject fluid through a nozzle 26 whose tip 32 is angularly offset. A multi-piece construction that operates on a similar principle is disclosed in U.S. Pat. No. 5,516,008 entitled MEDICATION DISPENSING CONTAINER. Finally, a right-angled tube extending from an ordinary eyedrop bottle is revealed in U.S. Pat. No. 3,756,478 entitled EYE DROP DISPENSER WITH LIQUID METERING DEVICE.

These patents reveal embodiments that require that the prevailing configuration of an eyedrop bottle that is available in the marketplace, namely, an elongated cylindrical shape with a funnel to an upright spout, be modified. Such modifications have not met with wide commercial acceptance, the reason being economic. The advantages from such modifications in ease of patient use apparently do not justify the additional costs or such modified versions would be widely available. The patient, therefore, is literally stuck using what's available, i.e., the conventional cylindrical eyedrop bottle funneling to an upright spout.

It would therefore be desirable to give the patient more options and to improve upon the conventional cylindrical eyedrop bottle funneling to an upright spout for dispensing eyedrops if the eyedrop bottle suppliers fail to do so.

BRIEF SUMMARY OF THE INVENTION

One aspect of the invention resides in a dispenser of eyedrop medication. The dispenser includes a detachable spout connected to a bottle. The spout has its discharge port offset from a center of the eyedrop bottle by a distance preferably exceeding one-half the width of the entrance port of the spout.

BRIEF DESCRIPTION OF THE SEVERAL VIEWS OF THE DRAWING

For a better understanding of the present invention, reference is made to the following description and accompanying drawings, while the scope of the invention is set forth in the appended claims.

DETAILED DESCRIPTION OF THE INVENTION

Figure 1:
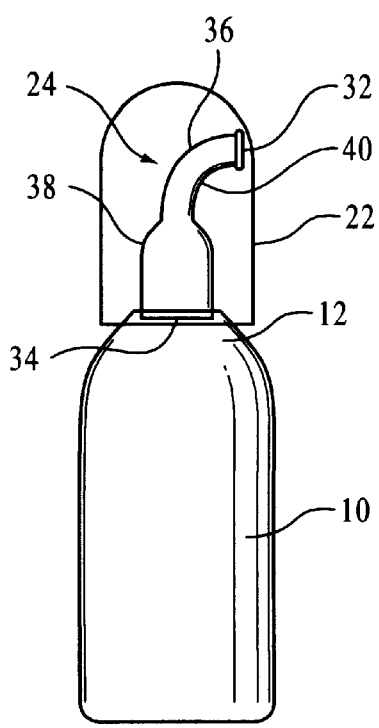
FIG. 1 shows a schematic representation of the present invention in accordance with a spout embodiment secured to a conventional eyedrop bottle and further showing the cap of the eyedrop bottle.

Turning to the drawings, FIGS. 1–9 each show a conventional eyedrop bottle 10 that is cylindrical in cross section together with a neck 12 of narrower diameter than the base of the eyedrop bottle 10. The neck terminates into an open end, which may be closed by a conventional spout configured for dispensement of the contents of the eyedrop bottle. Such a conventional spout 14 (FIGS. 3–4 and 7) has a straight funnel 16 and a discharge port 18 concentric with each other relative to an axial line 20.

Figure 2:
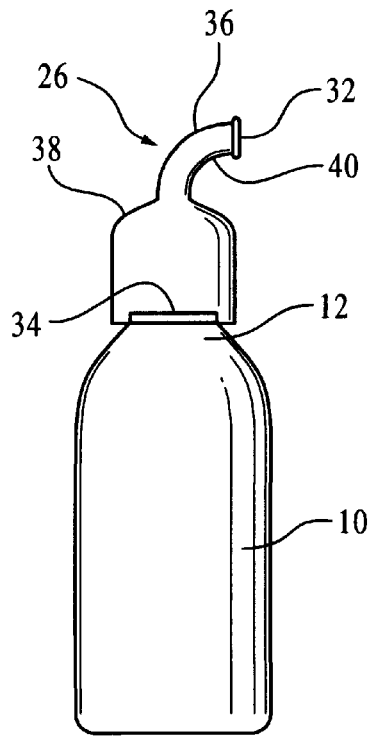
FIG. 2 shows a schematic representation of the present invention in accordance with a further spout embodiment secured to a conventional eyedrop bottle.
Figure 3:
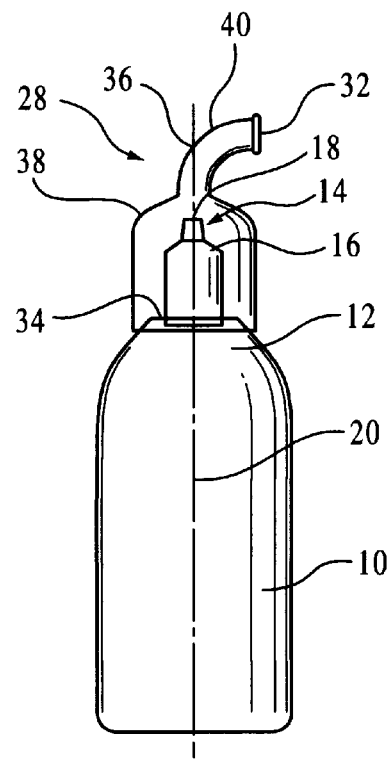
FIG. 3 shows a schematic representation of the present invention in accordance with another spout embodiment secured to a conventional eyedrop bottle.
Figure 4:
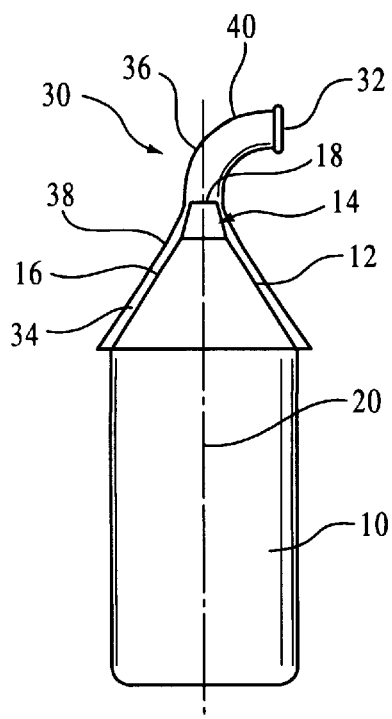
FIG. 4 shows a schematic representation of a further conventional eyedrop bottle with the spout embodiment of Fig. 3.
Figure 5:
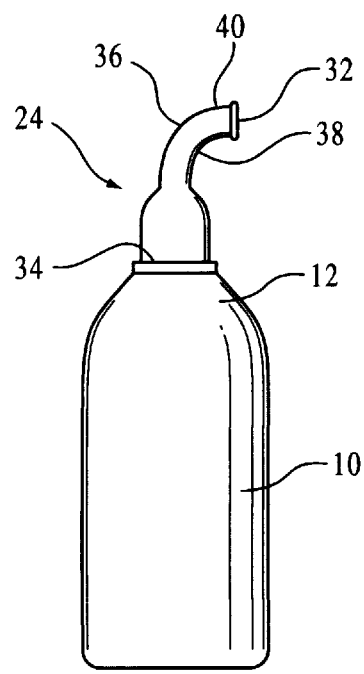
FIG. 5 shows a schematic representation of a further spout embodiment secured to a conventional eyedrop bottle.
Figure 6:
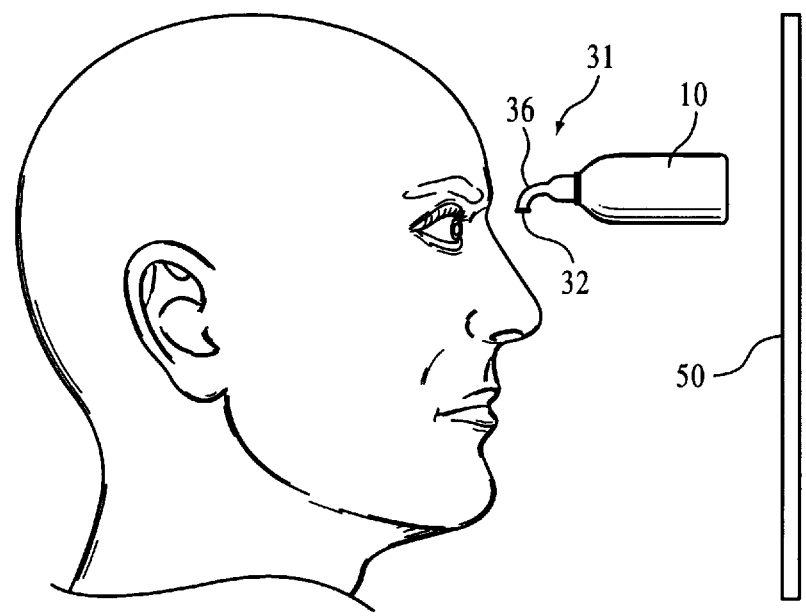
FIG. 6 shows a schematic representation of the bottle and spout of FIG. 5 in use by a patient arranged near a mirror.

Turning to FIG. 1, a cap 22 encloses a spout 24 in accordance with an embodiment of the invention. FIGS. 2–4 show spouts 26, 28 and 30, respectively. The cap 22 is connected to the exterior surface of the eyedrop bottle 10 at the open end of the bottle. FIG. 5 shows the embodiment of FIG. 1 without the cap 22. FIG. 6 shows spout 31.

In the case of FIGS. 1–6, the inventive spout 24, 26, 28, 30 and 31 as the case may be is shown with a discharge port 32, which is offset from the longitudinal center line 20 of the eyedrop bottle 10, and with an entrance port 34. Between these ports 32, 34 is a curved bend region 36. The curved bend region 34 includes a funnel 38 that terminates into the entrance port 34 and an extension 40 that terminates into the discharge port 32.

Preferably, the spout 24, 26, 28, and 30 is configured and arranged to be fully contained within the confines of the cap 22 for ensuring sterilization of the discharge port 32 while not in use. For this reason, the sideways length of the spout from the longitudinal center of the bottle should be less that the radius of the cap or, if longer as in the case of the spout 31 of FIG. 6, should be made of a flexible material that allows it to bend and thereby fit within the confines of the cap 22.

Such a flexible material should be elastic so that when the cap 22 is removed, the spout resiliently returns to its proper position for dispensing eyedrops. The flexible material may, for instance, be rubber, which may be treated, if necessary, with a flexible coating to protect the rubber from degrading or reacting with the medicinal contents of the bottle. Alternatively, the flexible material may be a flexible resin plastic that has a memory to return to its original configuration after the cap is removed and the spout is freed.

When squeezing the eyedrop bottle 10 to dispense its contents through the discharge port 32, the contents flow into the funnel 38, which is generally concentric with the longitudinal center line 20 of the eyedrop bottle 10. Then the contents flow through the curve of the curved bend region 36 to pass through the extension 40 and emerge to dispense through the discharge port 32.

The curved bend region 36 changes the direction of the flow of the eyedrop bottle, preferably so that the direction of flow through the extension 40 is in a direction generally transverse to the direction of flow through the funnel 38. The discharge port 32 is rounded to prevent corneal abrasion in the event that it comes into contact with the cornea of the eye.

FIG. 6 shows the manner in which the embodiments may be positioned for dispensing eyedrops from an eyedrop bottle 10. Although spout 31 is designated, any of the spouts 24, 26, 28 or 30 may be substituted.

As best seen in FIG. 6, the patient's head need not be tilted during eyedrop dispensement, The head may remain erect as the eyedrops are being dispensed. The discharge port 34 needs to be positioned adjacent the eye (FIG. 6) to ensure that all the dispensed drops to fall into the eye. The curvature of the curved bend region 36 (FIGS. 1–6, 8–9), however, enables the eyedrop bottle itself to be angled out of the line of sight 48 and thus into a position that does not block the view of a vertical mirror 50. The patient may then look into the mirror 50 as an aid in positioning the bottle for eyedrop dispensement.

Figure 7:
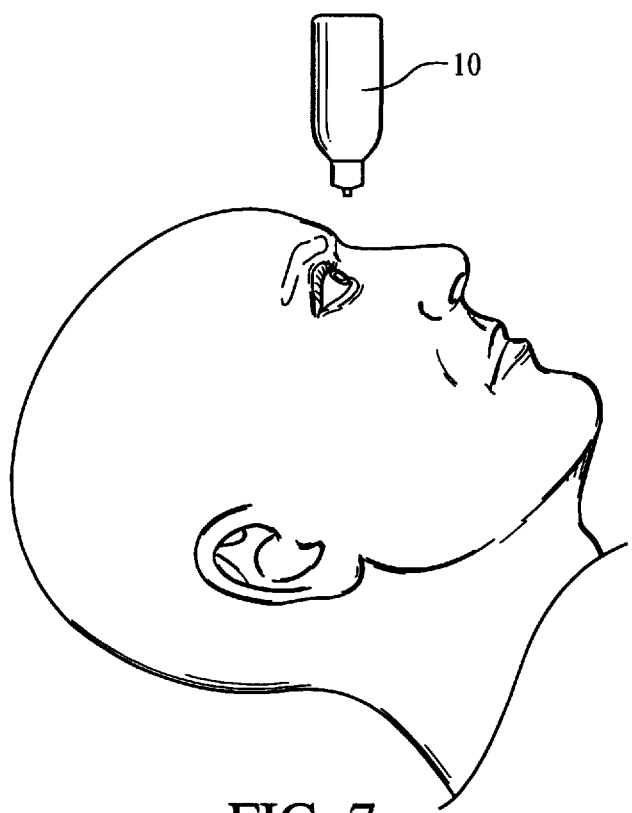
FIG. 7 shows a schematic representation of a conventional spout and eyedrop bottle in use by a patient arranged near a mirror.

FIG. 7, on the other hand, shows the conventional technique for dispensing eyedrops from a conventional eyedrop bottle whose spout is straight, requiring that the patient's head be angled to permit eyedrop dispensement. This arrangement prevents the patient from looking into a vertical mirror 50, because of the degree of head angulation that is required and because the line of sight becomes blocked from positioning of the eyedrop bottle 10 during its approach to the eye.

As can be appreciated from FIG. 6, the degree of head angulation required is significantly diminished relative to that of FIG. 7, if any is required at all. It is certainly less that what would hinder looking into the vertical mirror 50 during the approach of the eyedrop bottle 10 to the eye.

The securement of the spout 20 to the eyedrop bottle 10 may be effected in a number of different ways, i.e., through complementary engagement of mating elements, twisting engagement of threaded elements, resilient engagement by compressed elastic elements, or adhesive engagement. FIGS. 1 and 5 show connection between the entrance port 34 of the spout 24 and the inner surface of the open end of the bottle 10. FIGS. 2–4 show connection with the outside surface of the open end of the bottle 10.

Whether or not the spout 14 is integrally formed with the eyedrop bottle 10, the spout 28 may be fitted over the straight spout 14 to redirect the fluid flow after it emerges from the straight spout discharge port 18, i.e., to flow within the curved bend region 36 and along the extension 40 to emerge from the discharge port 32.

If such screw threads are not provided to facilitate securement of the spout to the outside of the bottle, other conventional fastening techniques may be used, such as the use of a wrap around clamp strap as exemplified by U.S. Pat. No. 5,724,021, whose contents are incorporated by reference as concerns a strap that clamps onto an eyedrop bottle.

The advantage of the spout in accordance with certain embodiments of the present invention where the spout may be detached from the bottle mouth is that the same spout may be used on any of a plurality of different kinds and types of eye drop bottles as long as the mouth of the eyedrop bottle is dimensioned to mate with the entrance port of the spout. Since eyedrop bottle mouths conventionally are made in standard sizes, a series of detachable spouts in accordance with the invention may be provided, each having a respective entrance port dimensioned to mate with the eyedrop bottle dimension of complementary dimension.

As an alternative, the spout itself could serve as an eyedrop bottle containing eyedrop medication. The only modification necessary is that the open entrance port 34 be closed.

For eyedrop dispensement, it is preferred that the eyedrop bottle 10 be swung to the side (away from in front of the eyes) so that only the discharge port 32 approaches the front of the eye, with the eyedrop bottle completely clear of the line of sight.

In the embodiments of FIGS. 1–5, the curved bend region 36 is responsible for defining a dimension in a radial direction from a center of the eyedrop bottle mouth to the discharge port 32 that is the same as or shorter than one half a width of the body of the eyedrop bottle. In the case of FIG. 7, this dimension exceeds the one half the width of the body of the eyedrop bottle.

The curved spout of any of the embodiments has additional advantages. As compared with an elongated and straight spout, for instance, the curved spout is less likely to result in one poking oneself in the eye. This may be attributed to the relative close proximity of the eyedrop bottle itself to the spout discharge port, which helps the eye judge relative distance, as compared to the opposite end of the elongated and straight spout that is grasped at that end.

Further, physicians may secure a patient's head between a chin rest and a forehead band and in front of a microscope having a lens. Thus, the chin rest and forehead define a space forward of the microscope that is approximately within the focal length of the lens of the microscope.

With the patient's head so secured and so close to the microscope, it is much easier for the physician to administer medication to the patient's eye from the curved spout than from a straight, elongated spout or from the conventional eyedrop bottle itself whose discharge opening is concentric with the bottle. The reason why it is easier is that the curved spout requires less room for maneuvering within the confined space constraints between the patient's face and the microscope, which does not give much room for the physician to maneuver elongated objects such as conventional bottles with straight spouts.

Figure 8:
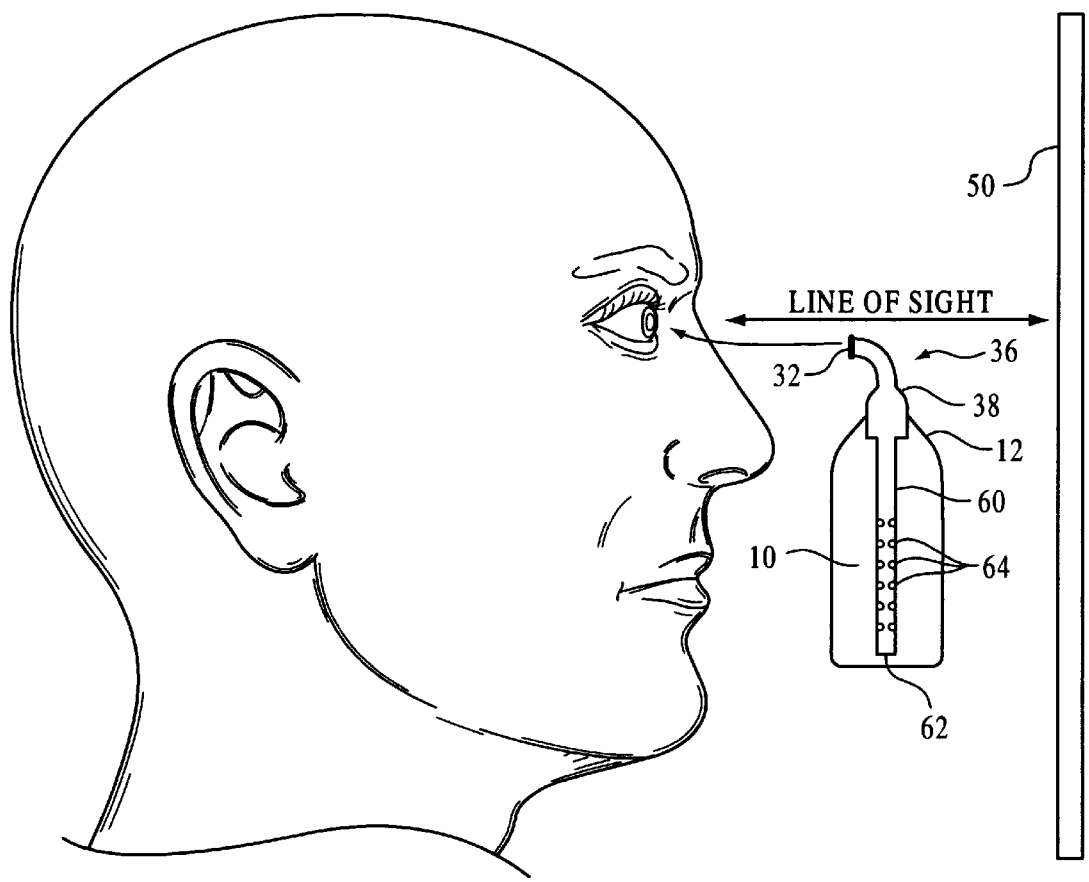
FIG. 8 shows a schematic representation of a further embodiment of the spout.

FIG. 8 shows a further embodiment that includes an elongated tube 60 that is open at its bottom 62 to permit medication egress and has fenestrations 64 or openings along its length to promote flow into the tube by the medication contents of the eyedrop bottle. This elongated tube may be extended in the manner shown in FIG. 8 from any of the embodiments of FIGS. 1–6 and is preferably integrally formed with the spout. The use of the elongated tube is advantageous in that it helps to concentrate the suction within the tube to ensure that all the contents of the eyedrop bottle will be dispensed.

Conventional eyedrop bottles that lack such a tube may retain residual eyedrop fluid at the bottom that may be wasted. Indeed, if a gravity assist is needed to help dispense the contents of the eyedrop bottle, then such positioning may adversely affect the ability of the user to position the eyedrop bottle optimally to avoid blockage with the line of sight toward a mirror. Such complications are avoided with the embodiment of FIG. 8 since there is a suction force that originates from the elongated tube 60 along its full length, as opposed to just at the mouth of the eyedrop bottle.

Figure 9:
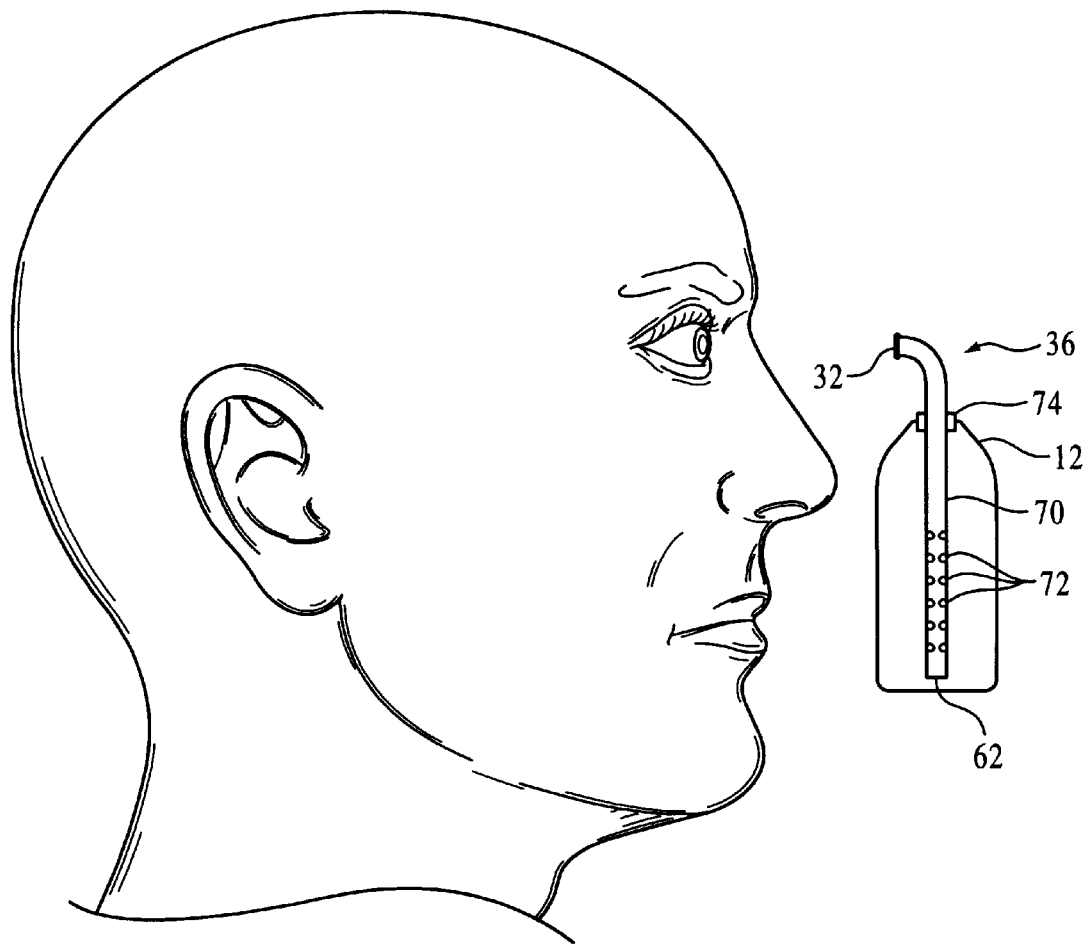
FIG. 9 shows a schematic representation of a another embodiment of the spout.

FIG. 9 shows a further variation of the embodiment of FIG. 8, but without the funnel. If the bottle opening is wider than the width of the elongated tube 70 that has fenestrations 72 in a manner analogous to that of the FIG. 8 embodiment, then a connecting piece 74 may be used to both grasp the elongated tube 70 and engage the threaded eyedrop bottle mouth connection in a liquid tight manner. The connecting piece 74 may be the same dimension as the funnel region of FIG. 8 and hollow (analogous to a tapered ring) to accommodate the elongated tube 70. The elongated tube would be connected to the connecting piece in any conventional manner, such as with fastening engagement, or may be formed as an elastic stopper held tightly in place to give a liquid-tight seal.

The embodiments of FIGS. 8 and 9, therefore, permit the eyedrop bottle to be held upright at all times during dispensement, even when very little remains within the eyedrop bottle. Further, medication that otherwise is trapped along the bottom of the eyedrop bottle if the suction force is too weak at the mouth of the eyedrop bottle, will be sucked out because the suction is kept concentrated along the length of the elongated tube that extends within the bottle.

The conventional eyedrop bottle 10 is made of a flexible material. The contents of the eyedrop bottle are forced to enter the spout 24, 26, 28, 30, 31 through the mouth in response to a squeezing of the eyedrop bottle on diametrically opposite locations on the exterior of the bottle. After entry into the spout, the contents flow through the curved bend region and then flow to dispense through the discharge opening. The opening is dimensioned to allow dispensement of eyedrops one at a time in response to the squeezing.

While the foregoing description and drawings represent the preferred embodiments of the present invention, it will be understood that various modifications may be made without departing from the spirit and scope of the present invention.

What is claimed is:

1. An eyedrop dispenser, comprising an eyedrop bottle with an open mouth, a spout having a funnel closing the mouth and terminating in a discharge port, the funnel having a curved bend region that changes a direction of flow of fluid passing from the mouth to the discharge port, the funnel narrowing in diameter from the mouth to the curved bend region, the eyedrop bottle having a body with a width that is larger that a dimension defined by twice a distance that the curved bend region extends in a radial direction from a center of the mouth to the discharge port, a cap that encloses the spout and is secured to the eyedrop bottle, the eyedrop bottle being made of a flexible material configured so that contents of the eyedrop bottle are forced to enter the spout through the mouth in response to a squeezing of the eyedrop bottle and thereafter are dispensed through the discharge port from the curved bend region.

2. An eyedrop dispenser as in claim 1, wherein said discharge port has a peripheral edge that is rounded.

3. An eyedrop dispenser as in claim 1, wherein said funnel has an inner facing surface configured with engaging portions that complement those on an outer facing surface of the mouth of the eyedrop bottle so as to mate therewith in a securing relationship.

4. An eyedrop dispenser spout as in claim 1, wherein said funnel has an outer facing surface configured with engaging portions that complement those on an inner facing surface of a mouth of the eyedrop bottle to mate therewith in a securing relationship.

5. An eyedrop dispenser as in claim 1, wherein said bottle contains eyedrop medication.

6. An eyedrop dispenser as in claim 1, wherein said curved bend region is made of a flexible material with a memory to resiliently return to an original position after being freed from being retained in a distorted position.

7. An eyedrop dispenser as in claim 1, further comprising an elongated tube extending from the funnel and away from the curved bend region, the elongated tube having a plurality of fenestrations spaced apart from each other along a length of the elongated tube.

8. An eyedrop dispenser, comprising an eyedrop bottle with an open mouth, a having a funnel closing the mouth and terminating in a discharge port, the funnel having a curved bend region that changes a direction of flow of fluid passing from the mouth to the discharge port, the funnel narrowing in diameter from the mouth to the curved bend region, and a cap that encloses the spout and is secured to the eyedrop bottle, said curved bend region being formed of a resilient material so that the discharge port moves between a distorted orientation as the cap is secured to the eyedrop bottle and a relaxed position as the spout is freed from the cap when the cap is removed from the eyedrop bottle, the eyedrop bottle being made of a flexible material configured so that contents of the eyedrop bottle are forced to enter the spout through the mouth in response to a squeezing of the eyedrop bottle and thereafter are dispensed through the discharge port form the curved bend region.

9. An eyedrop dispenser as in claim 8, wherein the body of the bottle contains eyedrop medication.

10. An eyedrop dispenser as in claim 8, wherein the eyedrop bottle has a further spout that is shrouded by a funnel of the curved bend region and that is configured to dispense contents of the eyedrop bottle into the curved bend region in response to forcing the contents to flow through the further spout.

11. An eyedrop dispenser spout as in claim 8, further comprising an elongated tube extending into the eyedrop bottle and away and from the curved bend region, the elongated tube having a plurality of fenstrations spaced apart along a length of the elongated tube.

12. An eyedrop dispenser, comprising:
an elongated tube having fenestrations spaced apart along a length of the elongated tube, a curved bend region, a discharge port, the curved bend region being between the elongated tube and the discharge port and being configured to change a direction of the contents of the flow from the elongated tube to the discharge port; and
an eyedrop bottle with an open mouth in which extends the elongated tube that allows the elongated tube to pass but is otherwise sealed, a spout having a funnel closing the mouth and terminating in the discharge port, wherein the funnel narrowing in diameter from the mouth to the curved bend region, the curved bend region changes the direction of the flow of the eyedrop bottle so that the direction of flow is in a direction generally transverse to the direction of the flow through the funnel, the eyedrop bottle being formed of a flexible material and configured so that contents of the eyedrop are forced to enter the spout from the mouth in response to a squeezing of the eyedrop bottle and thereafter are dispensed through the dispensing port from the curved bend region.

13. An eyedrop dispenser as in claim 12, further comprising a connection between the elongated tube and the mouth of the eyedrop bottle that engages the mouth of the eyedrop bottle to make a seal.

14. An eyedrop dispenser as in claim wherein the eyedrop bottle contains medication.

* * * * *